US00PP23721P3

(12) United States Plant Patent
Bradford

(10) Patent No.: US PP23,721 P3
(45) Date of Patent: Jul. 9, 2013

(54) CHERRY TREE NAMED 'ARVIN GLEN'

(50) Latin Name: *Prunus avium*
Varietal Denomination: ARVIN GLEN

(76) Inventor: Lowell Glen Bradford, Le Grand, CA (US)

( * ) Notice: Subject to any disclaimer, the term of this patent is extended or adjusted under 35 U.S.C. 154(b) by 77 days.

(21) Appl. No.: 13/374,007

(22) Filed: Dec. 8, 2011

(65) Prior Publication Data

US 2013/0152252 P1 Jun. 13, 2013

(51) Int. Cl.
*A01H 5/00* (2006.01)

(52) U.S. Cl.
USPC ..... Plt./181

(58) Field of Classification Search
USPC ..... Plt./181
See application file for complete search history.

(56) References Cited

U.S. PATENT DOCUMENTS

PP12,859 P2 8/2002 Bradford

*Primary Examiner* — Susan McCormick Ewoldt

(57) ABSTRACT

The present invention relates to a cherry tree, *Prunus avium,* and more particularly to a new and distinct variety broadly characterized by a medium size, moderately vigorous, hardy, self-unfruitful, very productive and regular bearing tree. The fruit matures under the ecological conditions described in mid May, with first picking on May 16, 2011. The fruit is uniformly large in size, sweet in flavor, somewhat oblate in shape, clingstone in type, firm in texture, pink in flesh color, and full red in skin color.

1 Drawing Sheet

Botanical classification: *Prunus avium.*
Varietal denomination: 'ARVIN GLEN'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits, usually to capture recessive traits. The present invention relates to a new and distinct variety of cherry tree, which has been denominated varietally as 'ARVIN GLEN'.

During the spring of 2001 I gathered fruit from several different unnamed cherry seedlings in my experimental orchard near Le Grand, Calif. in Merced County (San Joaquin Valley). The seeds from this fruit were removed, cracked, stratified, germinated, and grown as seedlings on their own root in my greenhouse, and upon reaching dormancy transplanted to a cultivated area of my experimental orchard described above. During the fruit evaluation season of 2005 I selected the present variety as a single tree from the group described above. Subsequent to origination of the present variety of cherry tree, I asexually reproduced it by budding and grafting in the experimental orchard described above, and such reproduction of plant and fruit characteristics were true to the original plant in all respects. The reproduction of the variety included the use of 'Colt' (unpatented) rootstock, upon which the present variety was compatible and true to type.

The present variety is most similar to the 'Glenred' (U.S. Plant Pat. No. 12,859) cherry by being self-unfruitful, and by producing cherries that are large in size, oblate in shape, firm in texture, dark red in skin color, and sweet in flavor, but is distinguished therefrom by blooming four days later and by producing cherries that are pink instead of dark red in flesh color and that mature about eight days later.

SUMMARY OF VARIETY

In summary, the present variety is characterized by a medium size, moderately vigorous, hardy, self-unfruitful, very productive and regular bearing tree. The fruit matures under the ecological conditions described in mid May, with first picking on May 16, 2011. The fruit is uniformly large in size, sweet in flavor, somewhat oblate in shape, clingstone in type, firm in texture, pink in flesh color, and full red in skin color.

DRAWING

The accompanying photograph displays four fruits with the stems attached, two whole fruits detached from the stems to exhibit the skin color and form, two half fruits sectioned to reveal the flesh and fibers, an individual stone, a typical tip shoot, and several leaves, all typical of the subject variety. Two insets are included to display the buds and blossoms during the flowering season.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., and was developed at the state of firm ripe on May 20, 2011, on a seven year old tree using 'Colt' rootstock (unpatented). All major color code designations are by reference to the Inter-Society Color Council, National Bureau of Standards. Common color names are also used occasionally.

PARENTAGE

Seed parent: Unknown.
Pollen parent: Unknown.

TREE

Size: Medium, reaching a height of 12' [3.66 m.] and a spread of 4' [1.22 m.] after seven growing seasons on Colt (unpatented) rootstock.
Vigor: Medium vigor, responding typically to irrigation and fertilization. The plant should be grown on a standard commercial rootstock for production purposes.
Growth: Upright and somewhat dense.
Form: Vase form.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Very productive.
Fertility: Self-unfruitful, must be pollinated by another appropriate early blooming cherry, such as 'Glenred' cherry (U.S. Plant Pat. No. 12,859).
Bearing: Regular bearer, with no crop failures observed.
Trunk:
*Size.*—Slender, reaching a maximum diameter of 3" [76.2 mm.] after the seventh growing season.
*Texture.*—Medium shaggy.
*Bark color.*—A Brownish gray [64. brGy] and Dark grayish reddish brown [47. d.gy.rBr] variegation.
*Lenticels.*—Approximate Number Per Square Inch: 6. Color: Brownish orange [54. brO]. Average Size: 3/16" [4.8 mm.] to 5/8" [15.9 mm.]. Shape: Elongated, eye-shaped.
Branches:
*Size.*—Diameter of main scaffold measured 12" above the crotch is 2½" [63.5 mm.]. Diameter of limb measured 12" above first fork is 1½" [38.1 mm.].
*Texture.*—Smooth on first and second year wood, increasing roughness with age.
*Color.*—1st Year Wood topside: Grayish red [19. gy.R]. 1st Year Wood underside: Brilliant yellow green [116. brill.YG]. 2nd Year Wood: A Light grayish reddish brown [45. l.gy.rBr] and Moderate reddish brown [43. m.rBr] variegation.
*Lenticels.*—Number Per Square Inch: About 12 on second year wood. Color: Light orange [52. l.O]. Size: 1/64" [0.4 mm.] to 1/16" [1.6 mm.]. Shape: Eye-shaped.
Leaves:
*Size.*—Large. Average Length: 5½" [139.7 mm.]. Average Width: 2 1/16" [52.4 mm.].
*Arrangement.*—Alternate.
*Thickness.*—Medium.
*Form.*—Oval.
*Apex.*—Acuminate.
*Base.*—Rounded.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Vein color.*—Pale yellow green [121. p.YG].
*Petiole.*—Average Length: 1 3/16" [30.2 mm.]. Average Thickness: 3/32" [2.4 mm.]. Color: Light yellow green [119. l.YG], often Very deep red [14. v.deep R] where exposed to direct sunlight.
*Stipules.*—Number: 2 per leaf at development stage. Average Length: 7/16" [11.1 mm.]. Color: Light yellow green [119. l.YG] becoming Deep reddish Brown [41. deep rBr] with age.
*Glands.*—Number: Mostly 2 per leaf. Position: Alternately positioned on the petiole just below the leaf blade. Size: Large. Form: Reniform. Color: Pale yellow green [121. p.YG] becoming Dark pink [6. d.Pk] with age.
*Leaf buds.*—Pointed, medium.
Flower buds:
*Hardiness.*—Hardy, with respect to central California winters.
*Diameter.*—Typically 5/16" [7.9 mm.] 3 days before bloom.
*Length.*—Typically 5/8" [15.9 mm.] 3 days before bloom.
*Form.*—Free.
*Surface.*—Non-pubescent.
*Tip color.*—White [263. white] with a Light pink [4. l.Pk] tinge on some.
Flowers: Perfect, complete, perigynous, usually a single pistil, typically about twenty stamens, five sepals and petal locations alternately positioned.
*Average flower diameter.*—1 7/16" [36.5 mm.].
*Number of petals.*—Usually five, very few have extra petals or fragments.
*Petal shape.*—Circular to slightly oval.
*Petal margin.*—Entire, wavy with occasional serrations.
*Average petal diameter.*—1 1/16" [17.5 mm.].
*Average petal length.*—1 1/16" [17.5 mm.].
*Petal apex.*—Rounded with a small notch on most.
*Petal base.*—Cuneate.
*Petal color.*—White [263. white].
*Anther color.*—Light yellow [86. l.Y].
*Stigma color.*—Light greenish yellow [101. l.gY].
*Sepal color.*—Grayish purplish red [262. gy.pR] over Strong yellow green [117. s.YG].
*Sepal length.*—5/16" [7.9 mm.].
*Sepal width.*—3/16" [4.8 mm.].
*Average pistil length.*—1 1/16" [17.5 mm.].
*Average stamen length.*—9/16" [14.3 mm.].
*Fragrance.*—Moderate.
*Pollen production.*—Moderate.
*Bloom density.*—Heavy.
*Blooming period.*—Early, four days after 'Glenred' cherry (U.S. Plant Pat. No. 12,859).
*Onset of bloom.*—One percent on Mar. 18, 2011.
*Date of full bloom.*—Mar. 31, 2011.
*Duration of bloom.*—Ten to twenty days, dependent on ambient temperature.
*Number per cluster.*—Usually 2 to 10, 6 average.

FRUIT

Maturity when described: Firm ripe, May 20, 2011.
Date of first picking: May 16, 2011.
Date of last picking: May 28, 2011.
Size: Uniform, medium.
*Average diameter axially.*—1" [25.4 mm.].
*Average diameter across cheek plane.*—1 3/16" [30.2 mm.].

*Average diameter across suture plane.*—15/16" [23.8 mm.].
*Typical weight.*—0.38 ounces [10.7 grams].
Form: Uniform, symmetrical, somewhat oblate.
*Longitudinal section form.*—Oval to round.
*Transverse section through diameter.*—Elliptical.
Suture: An inconspicuous line located in a shallow trough, extending from the base to the pistil point.
Ventral surface: Rounded, lipped slightly on both sides.
Lips: Equal.
Cavity: Flaring, circular, suture showing on one side.
*Depth.*—1/8" [3.2 mm.].
*Breadth.*—1/2" [12.7 mm.].
Base: Slightly truncate if viewed in the suture plane, cordate if viewed parallel to the suture.
Apex: Rounded.
Pistil point: An inconspicuous dot.
Stem: Medium.
*Average length.*—1 11/16" [42.9 mm.].
*Average width.*—1/16" [1.6 mm.].
Skin:
*Thickness.*—Medium.
*Surface.*—Smooth.
*Tenacity.*—Tenacious to the flesh.
*Astringency.*—Very slight.
*Tendency to crack.*—Less than average in rainy conditions, rare in dry seasons.
*Color.*—A Very deep red [14. v.deep R] smoothly blending into a Dark red [16. d.R].
Flesh:
*Color.*—Moderate yellowish pink [29. m.yPk] throughout.
*Surface of pit cavity.*—Covered with Light orange yellow [70. l.OY] broken fibers when twisted away from the stone.
*Amygdalin.*—Moderate.
*Juice.*—Abundant, rich.
*Juice color.*—Dark pink [6. d.Pk] to Moderate red [15. m.R].
*Texture.*—Firm, melting.
*Fibers.*—Abundant, fine, tender.
*Ripens.*—Fairly even.
*Flavor.*—A nice balance of acid and sugar, typically 18-20 brix.
*Aroma.*—Very slight.
*Eating quality.*—Very good.

STONE

Type: Clingstone.
Form: Oval.
Hilum: Narrow, oblong.
Base: Rounded.
Apex: Rounded.
Sides: Equal.
Surface: Fairly smooth.
External color of stone: Pale yellowish pink [31. p.yPk] when first removed.
Pit wall color when cracked: Pale yellowish pink [31. p.yPk].
Cavity surface color: Brownish pink [33. brPk].
Average pit wall thickness: 1/16" [1.6 mm.]
Average width: 3/8" [9.5 mm.].
Average length: 3/8" [9.5 mm.].
Average breadth: 5/16" [7.9 mm.].
Tendency to split: None.
Kernel:
*Form.*—Oval.
*Skin color.*—Pale yellow [89. p.Y] when first removed.
*Pellicle color.*—Grayish yellow [90. gy.Y].
*Vein color.*—Grayish yellow [90. gy.Y].
*Taste.*—Bitter.
*Viable.*—Yes.
*Average width.*—3/16" [4.8 mm.].
*Average length.*—1/4" [6.4 mm.].
*Amygdalin.*—Abundant.

USE

Market: Fresh market and long distance shipping.
Keeping quality: Good, fruit quality observed to remain in good condition after 21 days in standard cold room at 34° Fahrenheit [1° Celsius].
Shipping quality: Good.
Resistance to insects: No unusual susceptibilities noted.
Resistance to diseases: No unusual susceptibilities noted.

OTHER NOTES

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of cherry tree, substantially as illustrated and described, that is most similar to the 'Glenred' (U.S. Plant Pat. No. 12,859) cherry by being self-unfruitful, and by producing cherries that are large in size, oblate in shape, firm in texture, dark red in skin color, and sweet in flavor, but is distinguished therefrom by blooming four days later and by producing cherries that are pink instead of dark red in flesh color and that mature about eight days later.

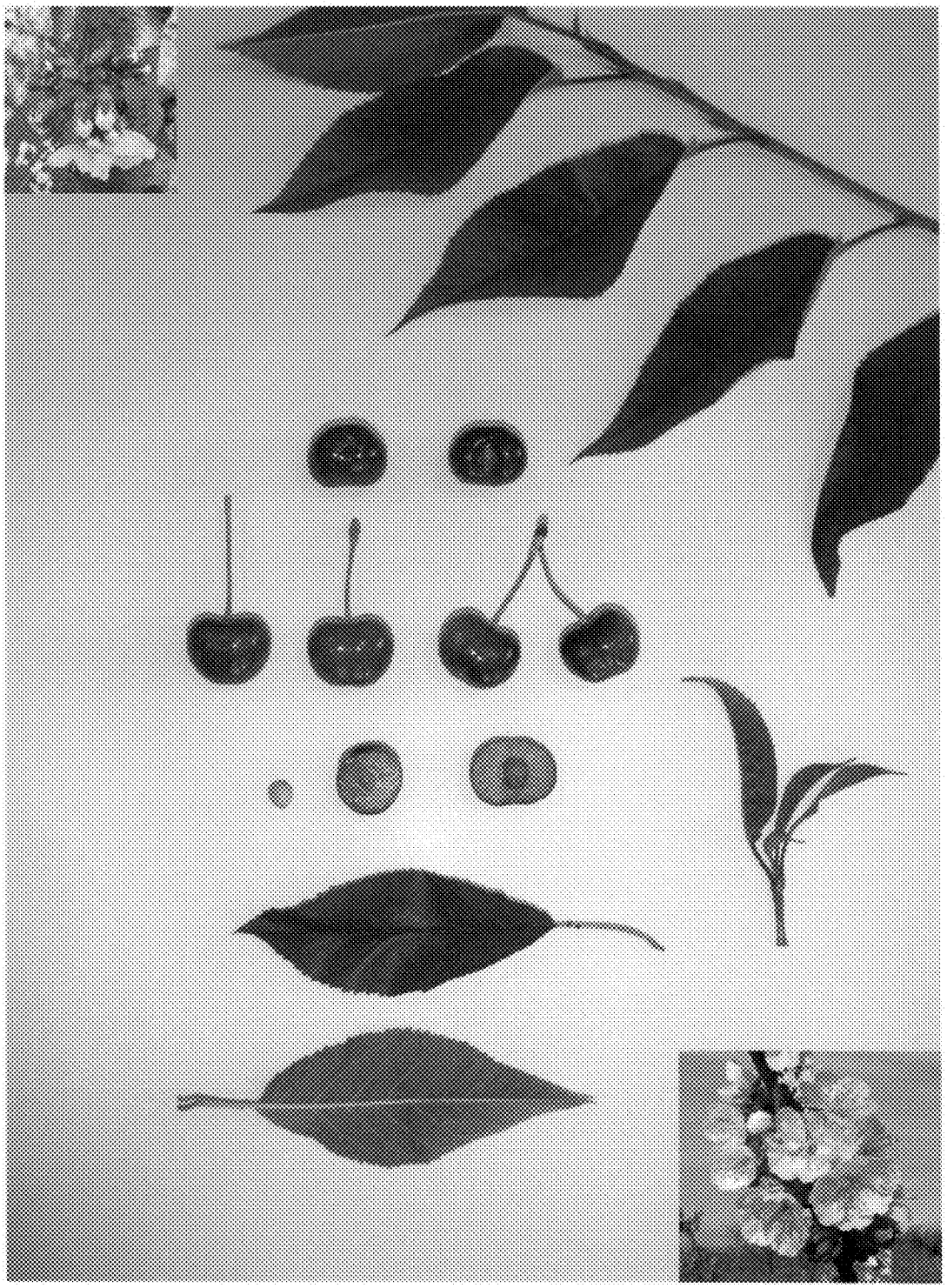

* * * * *